(12) United States Patent
Matsuo et al.

(10) Patent No.: US 6,727,355 B2
(45) Date of Patent: Apr. 27, 2004

(54) PHARMACEUTICAL COMPOSITION FOR TREATMENT OF DUCHENNE MUSCULAR DYSTROPHY

(75) Inventors: Masafumi Matsuo, 3-31, Kitaochiai 5-chome, Suma-kum, Kobe-shi, Hyogo 654-0151 (JP); Shoichiro Kamei, Hyogo (JP)

(73) Assignees: JCR Pharmaceuticals Co., Ltd., Hyogo (JP); Masafumi Matsuo, Hyogo (JP)

( * ) Notice: Subject to any disclaimer, the term of this patent is extended or adjusted under 35 U.S.C. 154(b) by 21 days.

(21) Appl. No.: 09/930,251

(22) Filed: Aug. 16, 2001

(65) Prior Publication Data

US 2002/0055481 A1 May 9, 2002

(30) Foreign Application Priority Data

Aug. 25, 2000 (JP) ........................................ 2000-256547

(51) Int. Cl.⁷ ........................... C07H 21/04; C12Q 1/68; C12P 19/34

(52) U.S. Cl. ................... 536/24.5; 536/24.3; 536/24.31; 536/24.33; 435/6; 435/91.1

(58) Field of Search .......................... 435/6, 91.1, 91.8, 435/325, 375; 536/23.1, 23.2, 24.5, 24.3, 24.31, 24.33; 514/44

(56) References Cited

U.S. PATENT DOCUMENTS

| | | |
|---|---|---|
| 5,151,510 A | 9/1992 | Stec et al. ................. 536/25.3 |
| 5,151,520 A | 9/1992 | Gottschalk et al. |
| 5,627,274 A | 5/1997 | Kole et al. |
| 5,665,593 A | 9/1997 | Kole et al. |
| 5,916,808 A | 6/1999 | Kole et al. |
| 5,948,680 A | 9/1999 | Baker et al. |
| 5,976,879 A | 11/1999 | Kole et al. |

FOREIGN PATENT DOCUMENTS

| | | |
|---|---|---|
| EP | 1054058 | 11/2000 |
| JP | 8-510130 | 10/1996 |
| JP | 2000-125448 | 4/2000 |
| JP | 2000-325085 | 11/2000 |
| JP | 2000-348957 | 12/2000 |
| WO | WO 89/06286 | * 12/1988 |
| WO | 94/26887 | 11/1994 |

OTHER PUBLICATIONS

DW Green et al., American College of Surgeons, "Antisense Oligonucleotides: An Evolving Technology for the Modulation of Gene Expression in Human Disease,"Jul. 2000, vol. 191, No. 1, pp. 93–105.*

K–Y Jen et al., Stern Cells, "Suppression of Gene Expression by Targeted Disruption of Messenger RNA: Available Options and Current Strategies," 2000, vol. 18, pp. 307–319.*

AD Branch, TIBS 23,"A good antisense molecule is hard to find," Feb. 1998, pp. 45–50.*

S. Agrawal et al., Molecular Medicine Today, "Antisense therapeutics: is it as simple as complementary base recognition?" Feb. 2000, vol. 6, pp. 72–81.*

JCT van Deutekorn et al., Human Molecular Genetics, "Antisense–induced exon skipping restores dystrophin expression in DMD patient derived muscle cells," 2001, vol. 10, No. 15, pp. 1547–1554.*

Crook, *Antisense Research and Application*, pp. 1–50 (Springer, New York).

Askari et al., *Molecular Medicine Antisense–Oligonucleotide Therapy*, N. Engl. J. Med., vol. 334, pp. 316–318 (1996).

Trojan et al., *Treatment and Prevention of Rat Glioblastoma by Immunogenic C6 Cells Expressing Antisense InsulinLike Growth Factor I RNA*, Science, vol. 259, pp. 94–97 (1993).

Trojan et al., *Loss of Tumorigenicity of Rat Glioblastoma Directed by Episome–Based Antisense cDNA Transcription of Insulin–Like Growth Factor I*, Proc. Nat. Acad. Sci. USA, vol. 89, pp. 4874–4878 (1992).

Ito et al., Am. J. Human Genetics, vol. 65, No. 4, p. A188 (Oct. 1999).

M. Koenig et al., "Complete Cloning of the Duchene Muscular Dystrophy (DMD) cDNA and Preliminary Genomic Organization of the DMD Gene in Normal and Affected Individuals", Cell, vol. 50, pp. 509–517 (1987).

Roland G. Roberts et al., "Exon Structure of the Human Dystrophin Gene", Genomics, vol. 16, pp. 536–538 (1993).

Hisahide Nishio et al., "Identification of a NovelFirst Exon in the Human Dystrophin Gene and of a New Promoter Located More than 500 kb Upstream of the Nearest Known Promoter", J. Clin. Invest., vol. 94, pp. 1037–1042 (1994).

Andrew H. Ahn et al., "The Structural and Functional Diversity of Dystrophin", Nature Genetics, vol. 3, pp. 283–291 (1993).

Vinita N. D'Souza et al., "A NOvel Dystrophin Insoform is Required for Normal Retinal Electrophysiology", Human Molecular Genetics, vol. 4, No. 5, pp. 837–842 (1995).

Eric P. Hoffman et al., "Dystrophin Abnormalities in Duchenne/Becker Muscular Dystrophy", Neuron, vol. 2, pp. 1019–1029 (1989).

(List continued on next page.)

Primary Examiner—Karen Lacourciere
(74) Attorney, Agent, or Firm—Greenblum & Bernstein, P.L.C.

(57) ABSTRACT

The invention provides an isolated and purified DNA set forth as SEQ ID NO:15 in the Sequence Listing and an antisense oligonucleotide complementary to the DNA. The DNA represents the splicing enhancer sequence (SES) in exon 45 of human dystrophin gene, and serves as a template in preparation of the antisense oligonucleotide, which is used to induce exon 45 skipping in certain group of patient with Duchenne muscular dystrophy to restore the reading frame of dystrophin mRNA.

2 Claims, No Drawings

OTHER PUBLICATIONS

Jeffrey S. Chamberlain et al., "Deletion Screening of the Duchenne Muscular Dystrophy Locus Via Multiples DNA Amplification", Nucleic Acids Research, vol. 16, No. 23, pp. 11141–11156 (1988).

Alan H. Beggs et al., "Detection of 98% of DMD/BMD Gene Deletions by Polymerase Chain Reaction", Human Genetics, vol. 86, pp. 45–48 (1990).

Grahame Bulfield et al., "X Chromosome–Linked Muscular Dystrophy (mdx) in the Mouse", Proc. Natl. Acad. Sci. USA, vol. 81, pp. 1189–1192 (1984).

Anthony P. Monaco et al., "An Explanation for the Phenotypic Differences Between Patients Bearing Partial Deletions of the DMD Locus", Genomics, vol. 2, pp. 90–95 (1988).

Jennifer Elizabeth Morgan, "Cell and Gene Therapy in Duchenne Muscular Dystrophy", Human Gene Therapy, vol. 5, pp. 165–173 (1994).

Louise V.B. Nicholson et al., "Dystrophin in Skeletal Muscle; II. Immunoreactivity in Patients with Xp21 Muscular Dystrophy", Journal of the Neurological Sciences, vol. 94, pp. 137–146 (1989).

Christopher J. Klein et al., "Somatic Reversion/Suppression in Duchenne Muscular Dystrophy (DMD): Evidence Supporting a Frame–restoring Mechanism in Rare Dystrophin-Positive Fibers", Am. J. Hum. Genet., vol. 50, pp. 950–959 (1992).

Stephen D. Wilton PhD. et al., "Dystrophin Gene Transcripts Skipping the mdx Mutation", Muscle and Nerve, vol. 20, pp. 728–734 (1997).

Hitoshi Sakuraba et al., "Invariant Exon Skipping in the Human α–Galactosidase A Pre–mRNA: A $g^{+1}$ to t Substitution in a 5'Splice Site Causing Fabry Disease", Genomics, vol. 12, pp. 643–650 (1992).

Masafumi Matsuo et al., "A Very Small Frame–Shifting Deletion Within Exon 19 of the Duchenne Muscular Dystrophy Gene", Biochemical and Biophysical Research Communications, vol. 170, No. 2, pp. 963–967 (1990).

Masafumi Matsuo et al., "Exon Skipping During Splicing of Dystrophin mRNA Precursor Due to an Intraexon Deletion in the Dystrophin Gene of Duchenne Muscular Dystrophy Kobe", J. Clin. Invest., vol. 87, pp. 2127–2131 (1991).

Yoko Hagiwara et al., "A Novel Point Mutation ($G^{-1}$ to T) in a 5' Splice Donor Site of Intron 13 of the Dystrophin Gene Results in Exon Skipping and is Responsible for Becker Muscular Dystrophy", Am. J. Hum. Genet., vol. 54, pp. 53–61 (1994).

Masafumi Matsuo et al, "Partial Deletion of a Dystrophin Gene Lease to Exon Skipping and to Loss of an Intra–Exon Hairpin Structure from the Predicted mRNA Precursor", Biochemical and Biophysical Research Communications, vol. 182, No. 2, pp. 495–500 (1992).

Harry C. Dietz et al., "The Skipping of Constitutive Exons in Vivo Induced by Nonsense Mutations", Science, vol. 259, pp. 680–683 (1993).

Yasuhiro Takeshima et al., "Modulation of In Vitro Splicing of the Upstream Intron by Modifying an Intra–Exon Sequence Which is Deleted from the Dystrophin Gene in Dystrophin Kobe", J. Clin. Invest., vol. 95, pp. 515–520 (1995).

Akiya Watakabe et al., "The Role of Exon Sequences in Splice Site Selection", Genes & Development, vol. 7, pp. 407–418 (1993).

Zacharias Aloysius Dwi Pramono et al., "Induction of Exon Skipping of the Dsytrophin Transcript in Lymphoblastoid Cells by Transfecting an Antisense Oligodeoxynucleotide Complementary to an Exon Recognition Sequence", Biochemical and Biophysical Research Communications, vol. 226, pp. 445–449 (1996).

Kunio Inoue et al., "Binding of the Drosphila Transformer and Transformer–2 Proteins to the Regulatory Elements of Doublesex Primary Transcript for Sex–specific RNA Processing", Proc. Natl. Acad. Sci. USA, vol. 89, pp. 8095–8096 (1992).

"Oligonucleotides an dAnalogues: A Practical Approach", F. Eckstein, Ed., pp. 87–108, Oxford University Press, Oxford England, 1991.

R. Russell Martin, "Chapter 21: Early Clinical Trials with Gem 91, A Systemic Oligodeoxynucleotide", Applied Antisense Olognucleotide Technology, pp. 387–393, 1998.

Matthew G. Dunckley et al., "Modification of Splicing inthe Dystrophin Gene in Cultured Mdx Muschle Cells by Antisense Oligoribonucleotides", Human Molecular Genetics, vol. 5, No. 1 pp. 1083–1090 (1995).

* cited by examiner

PHARMACEUTICAL COMPOSITION FOR TREATMENT OF DUCHENNE MUSCULAR DYSTROPHY

FIELD OF THE INVENTION

The present invention relates to pharmaceutical compositions for treatment of Duchenne muscular dystrophy, which pharmaceutical compositions are designed to correct an existing shift of the amino acid reading frame in dystrophin pre-mRNA, by inducing in a predetermined manner an exon skipping in the pre-mRNA having the shifted reading frame as a result of abnormalities in dystrophin gene. More specifically, the present invention relates to a splicing enhancer sequence (SES) in dystrophin gene which can be utilized for the preparation of pharmaceutical compositions for treatment of a specific type of Duchenne muscular dystrophy, as well as to antisense oligonucleotides against the splicing enhancer sequence, and therapeutic pharmaceutical compositions comprising such oligonucleotides.

BACKGROUND OF THE INVENTION

Diagnosis has become available today for hereditary diseases caused by abnormal splicing of pre-mRNA molecules. A so far intractable disease, muscular dystrophy, has thus come to draw particular attention. Muscular dystrophy is divided into two groups: Duchenne muscular dystrophy (DMD) and Becker muscular dystrophy (BMD). DMD is a hereditary muscular disease of the highest incidence, occurring in one in 3,500 live male births. Patients of DMD at first exhibit a lowered muscular power in their infancy, then suffer a constant progression of muscular atrophy thereafter, and eventually die at around the age of 20. It is in contrast to BMD, in which the onset of the disease is relatively late, somewhere in the adulthood, and though a mild loss of muscular power is observed after the onset of the disease, patients can live nearly a normal life. No drug is so far available for effective treatment of DMD, and therefore development of a drug for its treatment has been longed for by the patients across the world. In 1987, dystrophin gene, the causative gene of DMD, was found by means of retrospective genetics, and BMD also was found to result from abnormality in the same dystrophin gene [Koenig, M. et al., Cell, 50:509–517(1987)].

Dystrophin gene is located in the subregion 21 of the short arm of the X-chromosome. The size of the gene is 3.0 Mb, the largest known human gene. Despite that large size, only 14 kb regions in total of the dystrophin gene do encode the whole dystrophin protein, and those encoding regions are divided into no less than 79 exons which are distributed throughout the gene [Roberts, R G., et al., Genomics, 16:536–538(1993)]. The transcript of dystrophin gene, i.e. pre-mRNA, is spliced into the mature 14 kb mRNA. The gene has eight distinct promoter regions also distributed within the gene and they are responsible for production of distinct mRNAs, respectively [Nishio, H., et al., J. Clin. Invest., 94:1073–1042(1994), Ann, A H. and Kunkel, L M., Nature Genet., 3:283–291(1993), D'Souza, V N. et al., Hum. Mol. Genet., 4:837–842(1995)]. Thus, dystrophin gene and its transcript are structurally very complex.

Genetic diagnosis of DMD and BMD was performed by Southern blotting using fragments of dystrophin gene in early years, and then using cDNAs as probes. Thus, it was revealed that approximately six tenth of DMD/BMD patients have abnormalities such as large loss or multiplication in dystrophin gene [Hoffman, E P. and Kunkel, L M., Neuron, 2:1019–1029(1989)]. Most of the abnormalities found in the gene in DMD/BMD patients was a loss in the gene, with sizes of as big as several kb. As abnormalities in dystrophin gene detected by Southern blotting were concentrated on two "hot-spots" in the gene, multiplex PCR was designed for genetic diagnosis, which can conveniently identify a deletion using two PCR (polymerase chain reaction) systems by focusing on 19 exons in those hot-spots [Chamberlain J S., et al., Nucleic Acids Res., 16:11141–11156(1988), Beggs A H., et al., Hum. Genet., 86:45–48(1990)]. The multiplex PCR has become the most popular diagnosing method today, for it gives results in a short time and can detect 98% of genetic abnormalities which are detectable by Southern blotting.

There is known an animal model for DMD, mdx (X chromosome-linked muscular dystrophy) mice [Bulfield, G. et al., Proc. Natl. Acad. Sci. U.S.A., 81:1189–1192(1984)].

Due to a nonsense mutation within exon 23 of mouse dystrophin, the gene is inactivated in the mdx mice, i.e., translation is terminated within exon 23. No functional dystrophin molecule is expressed in mdx mice, while a trace of dystrophin-positive muscle fiber is detectable histochemically.

To the cause of the great difference in pathological conditions clinically observed between the two diseases, DMD and BMD, both resulting from apparently similar abnormalities in the same dystrophin gene, no explanation had been given until so-called frameshift hypothesis was proposed [Monaco, A P., et al., Genomics, 2:90–95(1988)]: In DMD, a partial deletion in the gene causes a shift of amino acids reading frame along the dystrophin mRNA (i.e., out-of-frame shift) and an eventually emerging stop codon puts an end to the dystrophin synthesis before completion. In contrast, in BMD, the reading frame is kept intact (i.e., in-frame) in spite of a partial deletion present in the gene and a dystrophin protein therefore is synthesized, though it differs in size from wild dystrophin. Analyses of dystrophin in patients' muscle demonstrated that dystrophin was lost in DMD while it occurred in BMD with an altered staining property. In addition, based on a comparison made of the phenotypes DMD/BMD with the types of reading frames deduced from the respective abnormalities in dystrophin gene, the frameshift hypothesis has been proved proper in more than 90% of the patients.

For a method for treatment of muscular dystrophy, introduction of functional dystrophin gene has been attempted through myoblasts implantation or utilizing plasmids or viral vectors [Morgan, J., Hum. Gene. Ther. 5:165–173 (1994)].

Dystrophin-positive muscle fibers are also found in many DMD patients [Nicholson, L. et al., J. Neurol. Sci., 94:137–146(1989)]. The dystrophin positive fibers found in DMD patients have been said to be produced through exon skipping [Klein, C. et al., Am. J. Hum. Genet., 50:950–959 (1992)]. In mdx mice, an in-frame dystrophin transcript was identified, in which an exon containing a major nonsense mutation had been skipped [Wilton, S. et al., Muscle Nerve, 20:728–734(1997)].

Introns-including genetic information which was transcribed from the gene receives splicing to remove the introns and thus mature mRNA is produced which exclusively consists of exon sequences. The mature mRNA is then translated along its reading frame to synthesize a protein strictly in consistent with the genetic information encoded in the gene. In the step of splicing in pre-mRNA, there exists a mechanism for precisely distinguishing introns from exons in the pre-mRNA nucleotide sequence. For this purpose, sequences in intron-exon boundaries are conserved in every gene according to certain rules, and thus known as consensus sequences.

Consensus sequences are known at three sites: a splice donor site at the 5' end of an intron (the site providing an exon-intron junction), a splice acceptor site at the 3' end of the intron, and a branch site.

For a number of diseases, it has been reported that substitution of just a single nucleotide in one of these consensus sequences would lead to abnormal splicing. This indicates that the consensus sequences are the keys to splicing [Sakuraba, H. et al., Genomics, 12: 643–650 (1992)].

The present inventors performed a PCR diagnosis of dystrophin gene abnormalities in DMD/BMD patients for the first time in Japan, and thereby demonstrated that there was no significant difference between Westerners and Japanese in the type of abnormalities in the gene, i.e., no significant racial difference existed. Though the gene abnormalities thus found by genetic diagnosis were, without exception, gigantic ones involving several kb to several hundred kb nucleotides, further analyses for the first time led to identification of the nucleotide sequence of the deleted part of a dystrophin gene. The result was reported along with the corresponding case named "dystrophin Kobe" [Matsuo, M, et al., Biochem. Biophys. Res. Commun., 170:963–967 (1990)].

The case with the gene abnormality named "dystrophin Kobe" is DMD case. The results of its multiplex PCR analyses revealed that no band corresponding to exon 19 was found at its expected position in amplified products of genomic DNA, apparently indicating loss of exon 19. However, in a reaction attempted to amplify the exon 19 region of the genomic DNA, exon 19 was detected as the amplification product, though it was smaller than its normal size, indicating that the disease was not brought about by a simple exon deletion which had been frequently observed in dystrophin gene. PCR amplification was performed on exon 19 region of dystrophin genes from the family members of the patient. The DNAs from his mother and younger sister gave, along with normal one, an amplification product of the same size as the patient's amplification product, indicating that the former two were carriers of this abnormal gene.

Then, sequencing of the abnormal amplification product obtained from the patient revealed that 52 nucleotides were lost from exon 19 that is made up of 88 nucleotides. The loss of these 52 nucleotides in the exon sequence would have lead to a shift of the reading frame in the dystrophin mRNA (rendering it out-of-frame), thus giving rise to a stop codon within exon 20. The result of the genetic diagnosis was consistent with the clinically given diagnosis, DMD.

Dystrophin mRNA from the patient was analyzed in order to examine the effect of the lost part of exon 19 identified in dystrophin Kobe on splicing, [Matsuo, M., et al., J. Clin. Invest., 87:2127–2131(1991)].

First, cDNA was prepared using mRNA from leukocytes of the patient and reverse transcriptase. The cDNA then was amplified by nested-PCR. Amplification of a region covering from exon 18 through exon 20 gave an amplified fragment, which was smaller than the size expected from the identified abnormality in the genome. This suggested a possibility that either the mRNA had different type of abnormality from the abnormality in genomic DNA, or there were some difference between the mRNAs from leukocytes and the muscular cells. Then, in order to make clear whether this mRNA abnormality was shared by the mRNA from muscular cells, a region covering from exon 18 through exon 20 was amplified by PCR using cDNA prepared from mRNA from the muscular cells as a template. The obtained product was the same as the amplification product of the region covering exon 18 through exon 20 from leukocytes.

Then, sequencing of the thus obtained small-sized abnormal amplification product revealed that entire exon 19 sequence was lost from dystrophin cDNA of the dystrophin Kobe patient, with exon 18 directly connected to exon 20. This result was not in agreement with the fact that the genomic exon 19 sequence lacked just 52 nucleotides, with the other 36 nucleotides remaining in place. This indicates that in dystrophin Kobe, an exon skipping took place in the maturation process of pre-mRNA by splicing out of the 36 nucleotides remaining in exon 19.

Not a small number of cases have been reported in which exon skipping occurs as a result of abnormality of a gene. It was reported for the first time by the present inventors that a point mutation in dystrophin gene caused an exon skipping [Hagiwara, Y., Am. J. Hum. Genet., 54:53–61(1994)]. All of these mutations of the gene causing exon skipping were those localized in consensus sequences, which determine the splicing sites as aforementioned.

In contrast, no abnormality was detected in consensus sequences in dystrophin Kobe, with 52 nucleotides found deleted just from "within" the exon. The reason of the exon skipping in the case, therefore, was unknown.

As the exon skipping found in dystrophin Kobe was not attributable to an abnormality in the primary structure of its DNA or pre-mRNA, the cause of the exon slipping was expected to reside in an abnormality in the secondary structure of its pre-mRNA. Its secondary structure therefore was subsequently analyzed. Analysis was done on computer using an algorithm by Zuker et al. designed for calculation of the secondary structure with energetically the most stable bonding of bases [Matsuo, M. et al., Biochem. Biophys. Res. Commun., 182:495–500(1992)]. According to an analysis of the 617 bases including nucleotide sequences of wild-type dystrophin exon 19 and the introns on both sides, the pre-mRNA had a relatively simple stem-loop structure. A characteristic intra-exon hairpin structure was noted, in which base pairs were made within the exon 19 sequence itself. In contrast, deduction made of the secondary structure of pre-mRNA from a sequence consisting of the dystrophin Kobe's exon with the 52-base intra-exon deletion and adjacent introns, gave a result greatly different from the result obtained with the wild type. The most notable feature with regard to dystrophin Kobe was that it had a simple stem structure in which the exon sequence made pairs only with an intron sequence. This result suggested that the intra-exon hairpin structure found in the wild type might be the factor characterizing the structure of the dystrophin exon.

Then, out of the 79 exons of dystrophin gene, 22 exons were chosen for which the nucleotide sequences of respective adjacent introns had been known, and the secondary structures of their pre-mRNA were analyzed. The results revealed that all of the exons analyzed had an intra-exon hairpin structure. Thus, the intra-exon hairpin structures were thought to be essential elements for those exons to function. These findings strongly suggested that the exon skipping found in dystrophin Kobe occurred due to the elimination of the corresponding intra-exon hairpin structure in its pre-mRNA. Also suggested by this was that some exon sequence itself played an important role in exon recognition during splicing.

Recently, it was reported that, in addition to an abnormality in the consensus sequences, an abnormal sequence within an exon could also cause exon skipping [Dietz, H C., et al., Science, 259:680–683(1993)]. Thus, attention has been drawn not only to the consensus sequences but also to sequences within exons as factors serving to determine splicing sites. These have findings are requiring correction to the conventional concept of splicing in molecular biology.

As a sequence within exon 19 was suggested to be important in determining the splicing site, an in vitro splicing system was constructed and a test was carried out to confirm this possibility [Takeshima, Y., et al., J. Clin. Invest., 95:515–520(1995), Japanese Patent Application No. H11140930]. First, a mini-gene was created consisting of exons 18 and 19 plus intron 18 of dystrophin gene. A radioisotope-labeled pre-mRNA was synthesized using the mini-gene. The pre-mRNA thus obtained was mixed with HeLa cell nucleus extract to allow in vitro splicing to proceed. Thus produced mature mRNA was separated by electrophoresis. In this reaction system, splicing occurred as normal with pre-mRNA having normal exon 19, giving rise to a mature mRNA, in which exons 18 and 19 were directly connected. When the exon 19 sequence was replaced with that of dystrophin Kobe, however, mature mRNA was not obtained. This indicated that the 52 nucleotide lost from exon 19 in dystrophin Kobe had an important role in splicing.

This abnormal splicing, however, might have been due to the "size" of exon 19 which was shortened to 36 nucleotides. Thus, an experiment was carried out in the same manner using a mini-gene in which the deleted sequence of exon 19 was inserted in the opposite orientation for making up for the loss. With this pre-mRNA, splicing took place, but only with a low efficiency. This result suggested that the efficiency of splicing is lowered with an abnormal intra-exon sequence even if such an exon has a normal size, and further suggested that it is the nucleotide sequence in the exon (not its size) that is critical.

Then, in order to examine the effect of intra-exon nucleotide sequences on splicing, pre-mRNAs were synthesized containing one of two different sequences inserted instead of the lost 52 nucleotides and their efficiency of splicing was determined. With two pre-mRNAs containing an inserted fragment of β-globin gene or ampicillin resistance gene, splicing was observed but with a very low efficiency. The β-globin gene insertion, however, led to a relatively high splicing efficiency compared with the insertion of the ampicillin resistance gene. The former nucleotide sequence was rich in purine bases. A purine-dominated sequence within an exon is thought to take part in exon recognition [Watanabe, A., et al., Genes Dev., 7:407–418(1993)].

These results of experiments demonstrated that not only consensus sequences but also a sequence within the downstream exon is involved in splicing, and thus introduced a new concept into processing of genetic information.

<Regulation of Splicing with Antisense Oligonucleotide>

Based on the above finding that a sequence within exon 19 of dystrophin gene is highly important for its splicing to take place, the inventors continued the study focusing on the possibility of artificially inducing splicing by disrupting the sequence. Thus, an 2'-O-methyl oligoRNA was synthesized which was complementary to the 31-nucleotide sequence set forth as SEQ ID NO:2 in the Sequence Listing that included the nucleotide sequence set forth under SEQ ID NO:1 in the Sequence Listing, which constituted part of the 52-nucleotide sequence lost in dystrophin Kobe. Using the aforementioned in vitro splicing system, assessment was made on the effect of this oligoRNA on splicing of pre-mRNA consisting of [exon 18]-[intron 18]-[exon 19]. The results showed that the splicing reaction was inhibited dependently on the amount of added antisense oligonucleotide and the duration of the reaction. Thus, it was for the first time proved experimentally that splicing of dystrophin could be inhibited by an antisense oligonucleotide. This then suggested that splicing reaction occurring in the nucleus could be artificially manipulated [Takeshima, Y. et al., J. Clin. Invest., 95:515–520(1995)].

<Regulation of Splicing within the Nucleus>

To examine whether it is also possible within the nucleus of living cells to regulate splicing of dystrophin pre-mRNA with the antisense oligonucleotide, the present inventors introduced into human normal lymphoblastoid cells an antisense oligoDNA having a nucleotide sequence complementary to the nucleotide sequence set forth as SEQ ID NO:2 in the Sequence Listing that included the nucleotide sequence set forth as SEQ ID NO:1, and then analyzed the dystrophin mature mRNA thus produced in the presence of the antisense oligoDNA [Zacharias A. D P. et al., B.B.R.C., 226:445–449(1996)]. Briefly, the antisense oligoDNA was mixed with LipofectAMINE and the mixture was added to the culture medium of the lymphoblastoid cells to introduce the oligoDNA into the nucleus. As a result, it was found that, despite the previous results obtained with the in vitro splicing system, skipping of exon 19 was induced in the human lymphoblastoid cells by the antisense oligoDNA against the nucleotide sequence of dystrophin exon 19, thus giving rise to a mRNA in which exon 18 is connected directly to exon 20. Extended duration of culture led to a complete induction of this exon skipping, thus exclusively providing a mRNA from which exon 19 was deleted. It was also confirmed that splicing process of the other exons was not affected by this antisense oligoDNA.

Antisense oligonucleotides (AOs) have so far been applied to regulate gene expression by inhibiting protein translation. AOs have also been used to attack a specific region within a DNA to inhibit its transcription by RNA polymerase II. Another approach has also been known in which an abnormal splicing of pre-mRNA is inhibited using an antisense oligonucleotide [Japanese Laid-open Patent Publication No. H8-510130]. As it does not induce ribonuclease H activity, phosphorothioate-2'-O-methyloligonucleotide has been used to block a shifted splicing site in the pre-mRNA in patients of thalasemia-based anemia to restore proper splicing.

<Therapeutic Application of Artificial Induction of Exon Skipping>

As noted above, DMD results from an abnormality which causes an out-of-frame shift of the amino acids reading frame of dystrophin mRNA. Should this abnormal reading frame be converted to an in-frame arrangement, then DMD would be converted to BMD, and therefore amelioration of the symptoms would be expected. Assuming a patient with a simple loss of exon 20, for example, his phenotype will be of DMD, since the simple loss of exon 20 consisting of 242 nucleotides naturally will cause a frameshift and thereby allowing a stop codon to emerge earlier in the process of translation, thus leading to incomplete synthesis of dystrophin. However, if exon 19 skipping could be artificially induced by administering to the patient an antisense oligonucleotide against exon 19 such as the one used in the aforementioned experiment, the reading frame could turn in-frame again because of the total loss of 330 nucleotides from the pre-mRNA due to the loss of 242 nucleotides of exon 20 plus 88 nucleotides of exon 19. Therefore, at least theoretically, DMD could be converted to BMD.

As mentioned above, however, dystrophin gene is structurally very complex and its pre-mRNA takes a complex secondary structure including a number of large introns to be spliced out, which secondary structure regulates the normal procession of splicing. Therefore, practical applicability was unpredictable as to; whether skipping of exon 19 could be induced as desired by an antisense oligonucleotide against exon 19 in myoblasts from a patient with simple deletion of exon 20 as in normal human lymphoblastoid cells; whether, assuming that exon 19 skipping successfully was induced, a shift of the mRNA reading frame, from out-of-frame to in-frame position, could take place without affecting the splicing-out of exon 20 or splicing at other sites in the pre-mRNA which already had an abnormality leading to splicing out of exon 20; or whether, assuming the in-frame conversion was achieved, thus produced mRNA could function to efficiently produce a dystrophin-like protein.

Upon this background, one of the present inventors demonstrated that splicing out of exon 19 can be induced with an antisense oligonucleotide against exon 19 in the cells of a DMD patient having complete loss of exon 20 in mature dystrophin mRNA, and that the existing shift of the reading frame along the mature dystrophin mRNA can thereby be corrected, thus converting the dystrophin-negative cells to positive ones. Based on the results, an agent for treatment of DMD has been disclosed [Japanese Laid-open Patent Application No. 11-140930].

It was thus demonstrated that, when added to the culture medium of myoblasts from a DMD patient having a simple loss of exon 20, an antisense oligonucleotide against dystrophin exon 19 was incorporated into the myoblasts and then into the nucleus, and led to restoration of the reading frame, which now turned back to the in-frame position from the former out-of-frame position although having entire loss of exon 19 and 20, thus producing a dystrophin of full length except for the deleted part encoded by exons 19 and 20. This result strongly suggest the possibility that, by administering an antisense oligonucleotide against exon 19 to a DMD patient having a simple loss of exon 20, the very serious DMD case can be converted to a milder BMD case.

Thus, in addition to the so-far known consensus sequences located in exon-intron boundaries, a splicing enhancer sequence (SES) within the exon plays an important role in determining the site of splicing when a pre-mRNA transcribed from the genome is spliced into a mature mRNA. As aforementioned, one of the present inventors identified an SES in exon 19 and further demonstrated that an antisense oligonucleotide against the SES can induce skipping of exon 19.

In further studies, by using an in vitro splicing system, the present inventors successfully identified new SESs set forth as SEQ ID NO:3 and NO:4 in the Sequence Listing within dystrophin exons 43 and 53. Based on those SES sequences, therapeutic agents for Duchenne muscular dystrophy was created containing antisense oligonucleotides complementary thereto, in particular, antisense oligonucleotides comprising nucleotide sequences set forth as SEQ ID NO:5 and NO:6 in the Sequence Listing [Japanese Patent Application No. 2000-125448 (abandoned) and Japanese Patent Application No. 2000-348957 (unpublished), in which a priority is claimed based on the former application]. These agents are intended for the treatment of the types of Duchenne muscular dystrophy which is caused by an alteration in the number of the nucleotides in the nucleotide sequences encoding one or more exons adjacent to exon 43 or 53 in human dystrophin mRNA, wherein the net of the alteration in the number of the nucleotides is expressed as a loss of (3×N+1) nucleotides, wherein N is zero or a natural number.

Thus, by correcting the existing shift of reading frame by induction of exon skipping in the process of splicing of dystrophin pre-mRNA, it will be possible to convert DMD to BMD, in the latter of which a dystrophin protein with partly restored function is produced. However, there will be a variety of mutation sites in dystrophin gene leading to DMD. Therefore, for providing treatment of DMD caused by respective mutations, it is necessary to identify SESs in further exons and thereby providing their respective antisense oligonucleotides. The objective of the present invention is to identify the SES in exon 45 and to provide thereupon an agent for treatment of DMA by inducing exon 45 skipping.

SUMMARY OF THE INVENTION

Upon the above background, the present inventors successfully identified a new SES within exon 45 of dystrophin gene, and thereupon created new means for treatment of Duchenne muscular dystrophy.

Thus the present invention provides an isolated and purified oligonucleotide selected from the group consisting of a DNA comprising the nucleotide sequence set forth as SEQ ID NO:15 in the Sequence Listing and an RNA comprising the nucleotide sequence complementary to the nucleotide sequence that in turn is complementary to the nucleotide sequence set forth as SEQ ID NO:15 in the Sequence Listing.

The RNA functions as the SES within exon 45 of human dystrophin pre-mRNA. The DNA and RNA are used as templates for production of antisense nucleotides as therapeutic agents for a type of Duchenne muscular dystrophy discussed below. The DNA or RNA may be isolated at least to such a degree needed to allow preparation of an antisense oligonucleotide complementary to the sequence set forth as SEQ ID NO:15 using the DNA or RNA as a template.

The present invention further provides an isolated and purified antisense oligonucleotide comprising the nucleotide sequence complementary to the nucleotide sequence set forth as SEQ ID NO:15 in the Sequence Listing.

The antisense oligonucleotides, when administered, can induce skipping of exon 45 in the splicing process of human dystrophin mRNA as they are complementary to the SES within exon 45 of human dystrophin mRNA. Therefore, these antisense oligonucleotides is useful as therapeutic agents against a particular type of Duchenne muscular dystrophy, based on correcting the shift of reading frame.

The antisense oligonucleotide may be a DNA or phosphorothioate DNA comprising the nucleotide sequence set forth as SEQ ID NO:19 in the Sequence Listing. The sequence is complementary to the SES and flanking sequences on both sides thereof within exon 45. Therefore, the DNA (or phosphorothioate DNA) comprising the sequence of interest more strongly hybridizes with exon 45's SES in the pre-mRNA to block its functions.

The present invention further provides use of an isolated and purified antisense oligonucleotide comprising the nucleotide sequence complementary to the nucleotide sequence set forth as SEQ ID NO:15 in the Sequence Listing for the manufacture of a pharmaceutical composition for treatment of Duchenne muscular dystrophy caused by an alteration in the number of the nucleotides in the nucleotide sequences encoding one or more exons adjacent to exon 45 in human dystrophin mRNA due to deletion of one or more nucleotides from the normal nucleotide sequences, wherein the net of the alteration in the number of the nucleotides is expressed as a loss of (3×N+1) nucleotides, wherein N is zero or a natural number. The antisense oligonucleotide may be the DNA or phosphorothioate DNA comprising the nucleotide sequence se forth as SEQ ID NO:19 in the Sequence Listing.

The present invention further provides a therapeutic pharmaceutical composition comprising one of those isolated and purified antisense oligonucleotides against the exon 45 SES in a pharmaceutically acceptable injectable medium. The therapeutic pharmaceutical composition is used for a type of Duchenne muscular dystrophy caused by an alteration in the number of the nucleotides in the nucleotide sequences encoding one or more exons adjacent to exon 45 in human dystrophin mRNA due to deletion of one or more nucleotides from the normal nucleotide sequences, wherein the net of the alteration in the number of the nucleotides is expressed as a loss of (3×N+1) nucleotides, wherein N is zero or a natural number.

Therefore, the present invention further provides a method for treatment of a human patient with Duchenne muscular dystrophy caused by an alteration in the number of the nucleotides in the nucleotide sequences encoding one or more exons adjacent to exon 45 in human dystrophin mRNA due to deletion of one or more nucleotides from the normal nucleotide sequences, wherein the net of the alteration in the number of the nucleotides is expressed as a loss of (3×N+1) nucleotides, wherein N is zero or a natural number, wherein the method comprises administering to the patient an therapeutically effective amount of an isolated and purified antisense oligonucleotide comprising the nucleotide sequence complementary to the nucleotide sequence set forth as SEQ ID NO:15 in the Sequence Listing in a pharmaceutically acceptable injectable medium. In the method of treatment, the antisense oligonucleotide may be selected preferably from the group consisting of a DNA or phosphorothioate DNA comprising the nucleotide sequence set forth as SEQ ID NO:15 in the Sequence Listing.

DETAILED DESCRIPTION OF THE INVENTION

In the present invention, "oligonucleotide" includes not only oligoDNA and oligoRNA but also a phosphorothioate analogue such as phosphorothioate oligoDNA. Phosphorothioate DNAs are nucleotides in which one or more oxygen atoms in the phosphate group are replaced with sulfur atoms. They are nucleotide analogues more resistant to various nucleotide decomposing enzymes and therefore widely used in the field of genetic engineering, e.g., for site specific substitution in genes. The method of their production, their properties and their various applications are well known to those skilled in the art. Phosphorothioate DNAs form base pairs in the same manner as natural DNAs do but are more resistant to various decomposing enzymes. Therefore, phosphorothioate DNA may be employed in the present invention with particular advantage. "Phosphorothioate analogue" herein is of a structure in which one or more phosphodiester groups between the nucleotides in a DNA chain are replaced with phosphorothioate groups.

The therapeutic pharmaceutical composition of the present invention preferably comprises 0.05–5 μmol/ml of the antisense oligonucleotide, 0.02–10 w/v % of at least one carbohydrate or polyalcohol, and 0.01–0.4 w/v % of at least one pharmaceutically acceptable surfactant. More preferably, the antisense oligonucleotide is contained at 0.1–1 μmoles/ml.

For the above carbohydrates, particularly preferred are monosaccharide and/or disaccharide. Examples of the carbohydrates and polyalcohols include glucose, galactose, mannose, lactose, maltose, mannitol, and sorbitol. They may be employed alone or in combination.

Examples of preferred surfactants include polyoxyethylene sorbitan mono- to tri-ester, alkyl phenyl polyoxyethylene, sodium taurocholate, sodium cholate, and polyalcohol esters. A particularly preferred one of them is polyoxyethylene sorbitan mono- to tri-ester, and particularly preferred esters are oleate, laurate, stearate, and palmitate. They may be employed alone or in combination.

The therapeutic pharmaceutical composition of the present invention more preferably comprises 0.03–0.09 M of at least one pharmaceutically acceptable neutral salt, such as sodium chloride, potassium chloride and/or calcium chloride, etc.

The therapeutic pharmaceutical composition of the present invention more preferably may further contain 0.002–0.05 M of a pharmaceutically acceptable buffering agent. Examples of preferable buffering agents include sodium citrate, sodium glycinate, sodium phosphate, and tris(hydroxymethyl)aminomethane. Such buffering agents may be employed alone or in combination.

The above therapeutic pharmaceutical composition may be supplied in liquid forms. However, considering for cases in which it has to be stored for a certain periods of time, it generally is preferred that they are provided in a lyophilized form, in order to stabilize the antisense oligonucleotide for preventing reduction of its therapeutic activity. Prior to use, such a composition is reconstituted, i.e., made back into a liquid form to be injected, by using a solvent (such as injectable distilled water). Therefore the therapeutic pharmaceutical composition of the present invention includes such a composition that is provided in lyophilized form, which is designed for reconstitution to make the concentrations of their ingredients fall within predetermined ranges prior to administration to the patient. For increasing solubility of such lyophilized compositions, albumin or amino acids like glycine may be added. In designing the lyophilized composition, solvents for reconstitution may be injectable distilled water or it may contain some ingredients other than the antisense oligonucleotide of the therapeutic pharmaceutical composition.

The present invention will be described in further detail below with reference to a set of tests conducted.

1. Induction of Exon Skipping in Lymphoblastoid Cells Derived from a Patient

As aforementioned, it was confirmed that the antisense oligonucleotide against the nucleotide sequence of dystrophin exon 19 efficiently induced skipping of the exon in the splicing reaction on the pre-mRNA transcribed from the dystrophin gene with normal structure. On the other hand, it is expected that the dystrophin pre-mRNA of a DMD patient with deleted exon 20 had abnormal secondary or tertiary structure, since its gene structure is different from that of the normal one. Thus, study was made to examine whether the above-mentioned 31-base antisense oligonucleotide would really work in such a DMD patient. Briefly, as will be described in detail below, EB virus-transformed lymphoblastoid cell lines were established from two DMD patients who lacked dystrophin exon 20. Using these cell lines it was confirmed that the antisense oligonucleotide can induce exon skipping.

(a) Establishment of Lymphoblastoid Cell Lines from DMD Patients

EB virus-transformed lymphoblastoid cell lines were established as follows from two DMD patients who lacked dystrophin exon 20: Two ml of whole blood taken from each of the patients was mixed with 2 ml of RPMI1640 medium (supplemented with 10% FBS) and loaded onto 3 ml of Ficoll Paque (Pharmacia) and then subjected to density-gradient centrifugation. The lymphocytes layer then was selectively collected, washed twice with RPMI1640 medium (supplemented with 10% FBS), and suspended in 0.5 ml of RPMI1640 medium (supplemented with 10% FBS) to give a lymphocytes suspension. This suspension was mixed with a 0.5 ml EB virus solution which had been prepared beforehand, and the mixture was cultured at 37° C. for a week. A week later, the culture was washed with RPMI1640 medium (supplemented with 10% FBS) in order to remove the EB virus, and culture was continued with the same medium. Thus, the lymphocytes from the patients were infected with EB virus and gave morphologically large, lymphoblastoid cells.

(b) Introduction of Antisense Oligonucleotide

The above obtained culture of lymphoblastoid cell lines was centrifuged to separate cellular component. The cells were cultured at 36° C. for 5 hrs in a maintenance medium containing about 200 nM (200 pmol/ml) of an antisense oligoDNA consisting of a 31-nucleotide sequence complementary to the nucleotide sequence set forth as SEQ ID NO:2 in the Sequence Listing and 2% fetal bovine serum (FBS). The medium then was replaced with a serum medium and culture was continued for additional 12 hrs. After the culture, the cells were collected and the whole RNAs extracted in a conventional manner.

(c) Analysis of Dystrophin cDNA

Using thus obtained whole RNAs as templates, cDNA were synthesized in a conventional manner by reverse transcriptase with random oligonucleotide primers consisting of hexaoligonucleotides. Using thus obtained cDNAs, a region covering dystrophin exon 18 through exon 21 was amplified by nested PCR. The first cycle of amplification was carried out using primers designed for exon 18 and exon 21. Using this amplification product as a template, the second PCR was carried out with primers designed to match to inner regions of those designed for the first primers. This amplification was done with the annealing temperature set at 60° C.

(d) Confirmation of Exon 19 Skipping

The amplification of the region covering exon 18 through exon 21 of dystrophin cDNA, when performed without addition of the antisense oligonucleotide, gave a clear band of 384 base pairs. Sequencing of this amplification product in a conventional manner confirmed that it consisted of exons 18, 19 and 21. This was in consistent with the result of genetic analysis done on the patient.

On the other hand, using cDNA prepared from the cells which had been treated with the antisense oligoDNA, a smaller-sized amplification product with intact reading frame was also obtained since the fourth day of culture together with an amplification product with the same size as one obtained from the cells in which no antisense oligoDNA was added. By the same method, the lymphoblastoid cells established from the case 2 also gave two types of bands. Sequencing of the smaller-sized ones of these amplification products revealed that exon 18 sequence was connected directly to that of exon 21, with exons 19 and 20 both deleted. This indicates that the treatment with the antisense oligonucleotide caused skipping of exon 19. On the other hand, lymphoblastoid cells established from a normal donor gave only a smaller-sized amplification product in which exon 19 only was skipped. Examination performed on the whole dystrophin cDNA amplified in 10 antibody regions revealed no fragment suggesting further abnormality in splicing.

(e) Discussion

The observed difference in the exon skipping-inducing effect of the antisense oligonucleotide between the normal subject and the DMD patient seemed to be attributable to a difference in the secondary or tertiary structure at or around exon 19 of the pre-mRNA. Efficiency of exon skipping induction was further determined for the DMD patients by applying the antisense oligonucleotide at different concentrations. However, no condition was found under which all the transcript underwent exon skipping as shown in the cells derived from the normal subject. This induction observed with the antisense oligonucleotide was not observed with a sense oligonucleotide or with an antisense oligonucleotides against other regions.

These results indicate that it is possible to correct the reading frame of dystrophin pre-mRNA by inducing an exon skipping through manipulation of its splicing process. It was still unknown, however, whether a mRNA with amino acid reading frame restored by such correction could efficiently synthesize the protein also in muscular cells.

2. Expression of Dystrophin-like Protein in Muscular Cells from DMD Patient

Then, examination was conducted on whether a dystrophin-like protein would be expressed in myoblasts from a DMD patient who lacked exon 20.

(a) Establishment of a Muscular Cell Line from DMD Patient

A specimen of muscular tissue was aseptically taken from a patient who lacked dystrophin gene exon 20. The tissue was minced and trypsinized to give dissociated cells. The cells were washed and then cultured in a growth medium (Ham-F10 supplemented with 20% FCS and 0.5% chicken embryo extract). For subcultivation, the muscular cells were cultured on cover slips placed in culture dishes. When the proportion of myoblasts reached about 80%, the medium was replaced with Fusion medium (DMEM supplemented with 2% HS) to induce differentiation into muscular cells.

(b) Introduction of Antisense OligoDNA

On the fourth day of induction of differentiation, antisense oligoDNA (200 pmol) was introduced into the cells using LipofectAMINE (6 μl), and further cultured for 3, 7 and 10 days.

(c) Immunohistochemical Staining of Dystrophin

After respective incubations, the cells were subjected to immunohistochemical staining using an antibody against the C-terminus of dystrophin. As a result, it was found that dystrophin staining turned positive in the cells in which no dystrophin staining had been detected initially. Dystrophin positive cells were found in any of the cultures. In addition, staining with an antibody against the N-terminal region of dystrophin also gave a similar result to that obtained with the C-terminal staining, thus confirming that the produced protein extended from the N-terminus to the C-terminus of dystrophin.

While dystrophin staining thus turned positive in the myoblasts treated with the antisense oligoDNA, dystrophin staining remained negative in myoblasts which was treated likewise but without addition of the antisense oligoDNA.

(d) Analysis of Dystrophin cDNA

RNA was extracted in a conventional manner from the above myoblast culture added with the antisense oligoDNA. After the synthesis of cDNA from the RNA thus obtained, a region covering dystrophin exons 18–21 was amplified as described above with regard to the extraction of RNA from lymphoblastoid cells.

The amplification product thus obtained was then sequenced by a conventional method. As a result, since the fourth day of culture, the in-frame amplification product was obtained, in which amino acids reading frame was restored by direct connection of the exon 18 sequence to that of exon 21.

Then the entire region of the cDNA prepared from the myoblasts cultured with the antisense oligoDNA was amplified by PCR in 10 different portions separately. Thus obtained amplified fragments were electrophoresed to determine their sizes in a conventional manner. As a result, no fragment was found suggesting abnormal splicing except for the skipping of exons 19 and 20. These results indicate that the obtained dystrophin mature mRNA was a reading frame-restored, full length mRNA except for the entire loss of exons 19 and 20.

3. Transfer of Antisense OligoDNA into the Nucleus

Then, for evidence supporting that the antisense oligoDNA had really entered the nucleus and functioned there, a fluorescence-labeled antisense oligoDNA was employed and its transfer into the nucleus was monitored.

The antisense oligoDNA used above was labeled with FITC (fluorescein isothiocyanate) by a conventional method, and its transfer into the nucleus was monitored. Briefly, muscular cells from a DMD patient was cultured in a growth medium (Ham-F10 supplemented with 20% FCS and 0.5% chicken embryo extract). The culture was performed on cover slips placed in culture dishes. When the cells became semiconfluent, the medium was replaced with Fusion medium (DMEM supplemented with 2% HS) to induce differentiation into the muscular cells. On the fourth day of induction of differentiation, the FITC-labeled antisense oligoDNA (200 pmol) was introduced into the cells using LipofectAMINE (6 $\mu$l), and 1, 2, 3, 7 and 10 days later, localization of FITC was monitored.

As a result, fluorescence signals were detected, which were localized in the nucleus. This provides a support that the antisense oligoDNA did enter the nucleus and caused skipping of exon 19's splicing.

As demonstrated by the above results of experiments, it is possible to make the myoblasts of a DMD patient to synthesize a protein corresponding to dystrophin, by restoring the amino acids reading frame into in-frame position. This indicates that it is possible to convert patients of very serious, so far incurable DMD, in particular those with simple loss of exon 20, to milder BMD patients.

4. Intraperitoneal Administration of Antisense Oligonucleotide to mdx Mice

Male 6 to 8-week old mdx mice were intraperitoneally injected with 20 mg/kg of the antisense oligonucleotide against dystrophin mRNA exon 19. Tow, four, seven and 14 days after the intraperitoneal administration, tissue samples were taken from the cardiac and skeletal muscles of the mice, and the mRNAs contained were extracted in a conventional manner. Using the mRNAs as templates, a region covering exons 18 to through 20 of dystrophin mRNA was amplified by RT-PCR, and the amplification products were separated by gel electrophoresis. The result clearly showed, two days after the administration, that a nucleotide fragment was produced, which consisted only of exons 18 and 20, with exon 19 skipped, with both of cardiac and skeletal muscle samples. The fragment was still noted, though weaker, four days after the administration. The results indicates that an antisense oligonucleotide against an exon in dystrophin pre-mRNA induces skipping of the exon in cardiac and skeletal muscle cells, not only in in vitro tests but also in a whole animal which has received the antisense oligonucleotide by injection.

To examine the localization over time of the administered antisense oligonucleotide in the skeletal muscle, mdx mice were intraperitoneally administered with 20 mg/kg of the FITC-labeled antisense oligonucleotide, and, tow, four, seven and 14 day after the administration, tissue samples were taken from the skeletal muscle of the mice and examined by a fluorescence microscope. As a result, the cell membranes of the skeletal muscle cells were found fluorescence positive two days after the intraperitoneal administration of the FITC-labeled antisense oligonucleotide. Since four days after the administration, fluorescence were also noted in the nucleus of the muscle cells. The result indicates that the injected oligonucleotide was transferred to the nucleus of the muscle cells.

To study the dose-response relation of the antisense oligonucleotide, dmx mice were intraperitoneally administered with 0.2, 2, 20 or 200 mg/kg, respectively, of the antisense oligonucleotide. Two days after the administration, tissue samples were taken from the cardiac and skeletal muscles and the mRNAs contained were extracted in a conventional manner. A region covering exon 18 through exon 20 was amplified by RT-PCR, and the amplification products were separated by gel electrophoresis. As a result, the nucleotide fragment consisting of exons 18 and 20, with exon 19 skipped, was clearly noted in the tissues of mice that received 20 mg/kg or 200 mg/kg of the antisense oligonucleotide. The production of the fragment was most remarkable with the sample from the mice that received 20 mg/kg of the antisense oligonucleotide.

5. Detection of SES in Other Exons-1

Based on the above results, the present inventors examined exons consisting of an odd number of nucleotides relative to a reading frame (therefore, loss of one of such exons would cause an out-of-frame reading of amino acids) in and around exons 45–55, the regions in dystrophin gene where high incidence of mutation is noted, for sequences which will give SESs as transcripts. According to an in vitro analysis, as aforementioned, SES is rich in purine nucleotides (in particular, repeats of sequence "AAG"). Based on this, the present inventors selected following three regions as candidates which could provide templates for transcripts relatively rich in purine nucleotides, and examined whether the sequences could give transcripts having SES activity: (1) a 26-nucleotide sequence (nucleotide sequence complementary to the nucleotide sequence set forth under SEQ ID NO:3) within exon 43, (2) a 28-nucleotide sequence within exon 46, and (3) a 26-nucleotide sequence within exon 53 (nucleotide sequence complementary to the nucleotide sequence set forth under SEQ ID NO:4).

For construction of pre-mRNA for the assessment of SES activity, the plasmid described in Watakabe, A., et al., Genes & Development, 7:407–418(1993) was employed as the standard plasmid, which included exon 3, intron 3 and a 5'-terminal region of exon 4 of Drosophila's doublesex (dsx) gene. This was a plasmid prepared by inserting into the BglII-SmaI site of plasmid pSP72 a BglII-HincII fragment from pSPdsxE34f [Inoue et al., Proc. Natl. Acad. Sci. USA, 89:8092–8096(1992)], which in turn was a plasmid prepared by subcloning into pSP73 (Promega) a genomic dsx fragment spanning from exon 3 to the site 1128 bp downstream of the female-specific acceptor site of Drosophila doublesex gene (dsx). The BglII-HincII fragment provides a system in which no splicing takes place between the exons flanking on both ends of intron 3 in the transcript unless an SES is added immediately downstream of the 5'-terminal region of exon 4, which is the female-specific exon, but splicing occurs when an SES is added at the position. For each of nucleotide sequences to be evaluated, single stranded, forward and reverse DNAs were synthesized separately. A BamHI cleaving site was added to the forward DNA at its 5'-terminus. A XhoI cleaving site was added to the reverse DNA at its 5'-terminus. The forward and reverse DNAs thus prepared were combined, heated (94° C., 2 min), and annealed at room temperature to obtain a double stranded DNA. The double stranded DNA was inserted into the BamHI-XhoI site located immediately downstream of the 5'-terminal region of dsx exon 4 in the standard plasmid for assessment described above. Thus, plasmids were obtained each of which included a mini-gene consisting of nucleotide sequence spanning from exon 3 to 5'-terminal region of exon 4 of dsx and a nucleotide sequence added downstream for evaluation. Radio isotope-labeled pre-mRNAs were prepared in a conventional manner with RNA polymerase using these plasmids as templates. These pre-mRNA then were reacted with a HeLa cell nucleus extract for 1 hr in the same manner as aforementioned to allow splicing, and the products were analyzed by gel electrophoresis in a conventional manner.

As a result, splicing reaction on the pre-mRNA having one of the SES candidates from 43 or 53 incorporated clearly gave a mRNA in which the exons on both sides of intron 3 had been spliced. This indicates that these two SES candidate sequences have SES activity. When compared between the two, SES activity was stronger with the candidate from exon 43. On the other hand, although the splicing reaction gave the spliced mRNA from the pre-mRNA having incorporated the exon 46 SES candidate, its activity was found very weak.

Thus, the present inventors revealed SESs within exons 43 and 53 of human dystrophin mRNA. Those SESs in the mRNA are the ribonucleotide sequences set forth as SEQ ID NO:3 and NO:4 in the Sequence Listing.

It has already been found by the present inventors that an SES is present in exon 19 of transcript pre-mRNA of dystrophin gene and that skipping of exon 19 can be induced by means of an antisense oligonucleotide against the SES, thereby restoring the reading frame. With regard to the additional SESs identified above within exons 43 and 53, respectively, their antisense oligonucleotides will induce skipping of exon 43 (173 nucleotides, i.e., 3×57+2 nucleotides) and exon 53 (212 nucleotides, i.e., 3×70+2 nucleotides), respectively.

Therefore, for a type of DMD case characterized by a reduction of (3×N+1) nucleotides (N is zero or a natural number) due to a loss of the nucleotides in one or more exons adjacent to exon 43 of dystrophin pre-mRNA, skipping of exon 43 will be induced during splicing by administering an antisense oligonucleotide against the SES within exon 43. By so doing, it is possible to correct the out-of-frame mutation and restore an in-frame structure, because the further loss of 173 nucleotides in exon 43 through splicing will make the total number of lost nucleotides in the spliced mRNA to be a multiple of 3. Thus, although the amino acids corresponding to the skipped nucleotide sequence will be lost, downstream amino acid sequence will become unaffected by the abnormality of the gene. A dystrophin will thus be synthesized, converting serious DMD to milder BMD. Examples of such DMD cases include those with the loss of exon 44 (148 nucleotides, i.e., 3×49+1 nucleotides), of exons 44 through 46 (148+176+148=472 nucleotides, i.e., 3×157+1 nucleotides), of exons 44 through 47 (148+176+148+150=622 nucleotides, i.e., 3×207+1 nucleotides), of exons 44 through 48 (148+176+148+150+186=808 nucleotides, i.e., 3×269+1 nucleotides), or of exons 44 through 49 (148+176+148+150+186+102=910 nucleotides, i.e., 3×303+1 nucleotides).

Similarly, for a DMD case which is characterized by a reduction of (3×N+1) nucleotides (N is zero or a natural number) due to a loss of nucleotides in one or more exons adjacent to exon 53 of dystrophin pre-mRNA, skipping of exon 53 during splicing will be induced by administering an antisense oligonucleotide against the SES within exon 53. Examples of such DMD cases include those with the loss of exon 52 (118 nucleotides, i.e., 3×39+1 nucleotides), of exons 50, 51 and 52 (109+233+118=460 nucleotides, i.e., 3×153+1 nucleotides). For these cases, by inducing exon 53 skipping during splicing through introduction of antisense oligonucleotide against the SES in exon 53, it is possible to modify the number of deleted nucleotides in the spliced mRNA into 330 or 672, respectively. By so doing, the number of deleted nucleotides in the spliced mRNA will become a multiple of 3 and therefore the existing shift of the reading frame caused by the original deletion will be corrected.

6. Detection of Further SES in Other Exons-2

The present inventors made a further study to identify an SES within exon 45 (whose nucleotide sequence is set forth as SEQ ID NO:7 in the Sequence Listing), which is in a region with high incidence of mutation in dystrophin gene. Briefly, a 163-nucleotide sequence prepared by deleting splicing sites (5'-terminal 7 nucleotides and 3'-terminal 6 nucleotides) of the exon 45 nucleotide sequence (176 bp) was divided into 5 fragments (Fragments 1–5), each of which consisted of about 30 nucleotides. The prepared fragments consisted of, in the order from 5'-terminus to 3'-terminus: 31 nucleotides (Fragment 1: set forth as SEQ ID NO:8 in the Sequence Listing), 32 nucleotides (Fragment 2: set forth as SEQ ID NO:9 in the Sequence Listing), 33 nucleotides (Fragment 3: set forth as SEQ ID NO:10 in the Sequence Listing), 32 nucleotides (Fragment 4: set forth as SEQ ID NO:11 in the Sequence Listing) and 35 nucleotides (Fragment 5: set forth as SEQ ID NO:12 in the Sequence Listing). Respective mini-genes were constructed as described above by introducing each of these DNA having template sequences for SES candidates into the 3'-terminal region of the plasmid having exon 3, intron 3 and a 5'-terminal region of exon 4 of Drosophila's doublesex (dsx) gene. For a positive control, a mini-gene was also constructed likewise in which the DNA having the exon 19 SES (set forth as SEQ ID NO:1 in the Sequence Listing) was incorporated. Using thus obtained SES activity assessing system, the SES activity was measured for each of the fragments. Briefly, radioisotope-labeled pre-mRNAs were synthesized by RNA polymerase using these plasmids as templates in a conventional manner. The respective pre-mRNAs were reacted with HeLa cell nucleus extract for one hour to allow splicing to proceed. After the splicing reaction, analysis was made by gel electrophoresis by a conventional method. As a result, it was found that Fragment 4 had a somewhat potent SES activity compared with other fragments.

Then, SES activity was assessed for sequences around Fragment 4. Briefly, from within the exon 45 nucleotide sequence, following fragments were prepared: 1) a fragment consisting of the nucleotides of the region with the same length and shifted upstream by 16bases (Fragment 4a: set forth as SEQ ID NO:13 in the Sequence Listing), 2) a fragment consisting of the nucleotides of the region with the same length and shifted upstream by 13 bases (Fragment 4b: set forth as SEQ ID NO:14 in the Sequence Listing), and a fragment consisting of the nucleotides of the region with the same length and shifted downstream by 16 bases (Fragment 4c: set forth as SEQ ID NO:15 in the Sequence Listing). For each fragment, SES activity was assessed as described above. As a result, Fragment 4c was found more potent than the original fragment, Fragment 4. The activity of Fragment 4c was as potent as that of exon 19 SES.

Then, SES activity was assessed for sequences around Fragment 4. Briefly, from within the exon 45 nucleotide sequence, following fragments were prepared: 1) a fragment consisting of the nucleotides of the region with the same length and shifted upstream by 16bases (Fragment 4a: set forth as SEQ ID NO:13 in the Sequence Listing), 2) a fragment consisting of the nucleotides of the region with the same length and shifted upstream by 13 bases (Fragment 4b: set forth as SEQ ID NO:14 in the Sequence Listing), and a fragment consisting of the nucleotides of the region with the same length and shifted downstream by 16 bases (Fragment 4c: set forth as SEQ ID NO:15 in the Sequence Listing). For each fragment, SES activity was assessed as described above. As a result, Fragment 4c was found more potent than the original fragment, Fragment 4. The activity of Fragment 4c was as potent as that of exon 19 SES.

Exon 45 consists of 176 nucleotides (3×58+2 nucleotides). Therefore, restoration of the reading frame will be made by inducing further loss of 176 nucleotides by skipping of exon 45 in a type of Duchenne muscular dystrophy caused by an alteration in the number of the nucleotides in the nucleotide sequences encoding one or more exons adjacent to exon 45 in human dystrophin mRNA due to deletion of one or more nucleotides from the normal nucleotide sequences, wherein the net of the alteration in the number of the nucleotides is expressed as a loss of (3×N+1) nucleotides, wherein N is zero or a natural number. Examples of such DMD cases include; a case with deletion of exon 44 (148 nucleotides, i.e., 3×49+1 nucleotides), a case with deletion of exon 46 (148 nucleotides, i.e., 3×49+1 nucleotides), a case with deletion of exons 46 and 47 (148+158=298 nucleotides, i.e., 3×99+1 nucleotides), a case with deletion of exons 46 through 48 (148+150+186=484 nucleotides, i.e., 3×161+1 nucleotides), a case with deletion of exons 46, 47 and 49 (148+150+102=400 nucleotides, i.e., 3×133+1 nucleotides), a case with deletion of exon 46, 47, 49, 50 and 51 (148+150+102+109+233=742 nucleotides, i.e., 3×247+1 nucleotides), and a case with deletion of 46, 47, 49, 50, 51, 52, 53, 54 and 55 (148+150+102+109+233+118+212+155+190=1417 nucleotides, i.e., 3×472+1 nucleotides).

DNAs and phosphorothioate oligoDNAs having a nucleotide sequence complementary to the nucleotide sequence set forth as SEQ ID NO:15 in the Sequence Listing may be produced using a commercially available DNA synthesizer such as Applied Biosystems Model 1380B, and according to the method described in Zon et al., [Oligonucleotides and Analogues: A Practical Approach, F. Eckstein, Ed., p.87–108, Oxford University Press, Oxford, England; U.S. Pat. No. 5,151,510].

7. Clinical Application of Antisense Oligonucleotide Against Exon 45 SES

An antisense oligonucleotide of the present invention will be administered to a corresponding DMD patient as follows. An antisense oligoDNA or an antisense phosphorothioate oligoDNA comprising the nucleotide sequence complementary to the nucleotide sequence set forth as SEQ ID NO:15, e.g., the antisense oligoDNA set forth as SEQ ID NO:19 in the Sequence Listing or an antisense phosphorothioate oligoDNA having the same nucleotide sequence, is produced by a conventional method well known to those skilled in the art, and sterilized by a conventional method and formed into, for example, a 1200 μg/ml injectable solution. The solution is then intravenously administered to a patient, for example by dropwise infusion of a parenteral fluid, at a dose of, for example, 20 mg of the antisense oligonucleotide per kg body weight. The administration is made four times at two-week intervals, for example. Later administration is repeated as needed while monitoring expression of the dystrophin protein in muscle tissue biopsy samples, serum creatine kinase levels, and therapeutic effect assessed on the basis of clinical symptoms. As far as it is therapeutically effective without an apparent side effect, the therapy is generally continued through the life of the patient.

The present invention is described in further detail below with reference to examples. It is not intended, however, that the scope of the present invention be restricted by the examples.

EXAMPLES

Composition Example 1

According to the following formula, necessary amount of respective base components are admixed to dissolve. The antisense oligonucleotide then is dissolved in the solution, the solution is made to volume and filtered through a membrane filter with a pore size of 0.22 μm to obtain a composition for intravenous administration.

| | |
|---|---|
| Antisense oligonucleotide (*1) | 500 mg |
| Sodium chloride | 8.6 g |
| Potassium chloride | 0.3 g |
| Calcium chloride | 0.33 g |
| Distilled water for injection | to 1000 ml |

*1: phosphorothioate oligoDNA consisting of a nucleotide sequence set forth as SEQ ID NO: 19 in the Sequence Listing

Composition Example 2

According to the following formula, necessary amount of respective base components are admixed to dissolve. The antisense oligonucleotide then is dissolved in the solution, the solution is made to volume and filtered through a filter with a pore size of 15 nm (PLANOVE 15: Asahi Chemical Industry Co., Ltd.) to obtain a composition for intravenous administration.

| | |
|---|---|
| Antisense oligonucleotide (*2) | 100 mg |
| Sodium chloride | 8.3 g |
| Potassium chloride | 0.3 g |
| Calcium chloride | 0.33 g |
| Sodium hydrogen phosphate · 12H$_2$O | 1.8 g |
| 1N hydrochloric acid | q.s. (pH 7.4) |
| Distilled water for injection | to 1000 ml |

*2: phosphorothioate oligoDNA consisting of a nucleotide sequence set forth as SEQ ID NO: 19 in the Sequence Listing

Composition Example 3

According to the following formula, necessary amount of respective base components are admixed to dissolve. The antisense oligonucleotide then is dissolved in the solution, the solution is made to volume and filtered through a filter with a pore size of 35 nm (PLANOVE 35: Asahi Chemical Industry Co., Ltd.) to obtain a composition for intravenous administration.

| | |
|---|---|
| Antisense oligonucleotide (*3) | 100 mg |
| Sodium chloride | 8.3 g |
| Potassium chloride | 0.3 g |
| Calcium chloride | 0.33 g |
| Glucose | 0.4 g |
| Sodium hydrogen phosphate · 12H$_2$O | 1.8 g |
| 1N hydrochloric acid | q.s. (pH 7.4) |
| Injectable distilled water | to 1000 ml |

*3: phosphorothioate oligoDNA consisting of a nucleotide sequence set forth as SEQ ID NO: 19 in the Sequence Listing

What is claimed is:

1. An isolated and purified oligonucleotide selected from the group consisting of:
   a DNA consisting of a nucleotide sequence set forth as SEQ ID NO:15 in the Sequence Listing, and
   an RNA consisting of a nucleotide sequence set forth as SEQ ID NO:15 in the Sequence Listing in which all thymine nucleotides are replaced by uracil.

2. An isolated and purified antisense oligonucleotide consisting of a nucleotide sequence fully complementary to the nucleotide sequence set forth as SEQ ID NO:15 in the Sequence Listing.

* * * * *

SEQUENCE LISTING

<160> NUMBER OF SEQ ID NOS: 19

<210> SEQ ID NO 1
<211> LENGTH: 16
<212> TYPE: DNA
<213> ORGANISM: Homo sapiens

<400> SEQUENCE: 1
gcaagatgcc agcaga                                                      16

<210> SEQ ID NO 2
<211> LENGTH: 31
<212> TYPE: DNA
<213> ORGANISM: Homo sapiens

<400> SEQUENCE: 2
aactgcaaga tgccagcaga tcagctcagg c                                     31

<210> SEQ ID NO 3
<211> LENGTH: 26
<212> TYPE: RNA
<213> ORGANISM: Homo sapiens

<400> SEQUENCE: 3
agcaagaaga cagcagcauu gcaaag                                           26

<210> SEQ ID NO 4
<211> LENGTH: 26
<212> TYPE: RNA
<213> ORGANISM: Homo sapiens

<400> SEQUENCE: 4
ggaagcuaag gaagaagcug agcagg                                           26

<210> SEQ ID NO 5
<211> LENGTH: 31
<212> TYPE: DNA
<213> ORGANISM: Homo sapiens

<400> SEQUENCE: 5
gcactttgca atgctgctgt cttcttgcta t                                     31

<210> SEQ ID NO 6
<211> LENGTH: 31
<212> TYPE: DNA
<213> ORGANISM: Homo sapiens

<400> SEQUENCE: 6
gacctgctca gcttcttcct tagcttccag c                                     31

<210> SEQ ID NO 7
<211> LENGTH: 176
<212> TYPE: DNA
<213> ORGANISM: Homo sapiens

<400> SEQUENCE: 7
gaactccagg atggcattgg gcagcggcaa actgttgtca gaacattgaa tgcaactggg      60
gaagaaataa ttcagcaatc ctcaaaaaca gatgcaagta ttctacagga aaaattggga     120
agcctgaatc tgcggtggca ggaggtctgc aaacagctgt cagacagaaa aaagag         176

```
<210> SEQ ID NO 8
<211> LENGTH: 31
<212> TYPE: DNA
<213> ORGANISM: Homo sapiens

<400> SEQUENCE: 8
aggatggcat tgggcagcgg caaactgttg t                            31

<210> SEQ ID NO 9
<211> LENGTH: 32
<212> TYPE: DNA
<213> ORGANISM: Homo sapiens

<400> SEQUENCE: 9
cagaacattg aatgcaactg gggaagaaat aa                           32

<210> SEQ ID NO 10
<211> LENGTH: 33
<212> TYPE: DNA
<213> ORGANISM: Homo sapiens

<400> SEQUENCE: 10
ttcagcaatc ctcaaaaaca gatgccagta ttc                          33

<210> SEQ ID NO 11
<211> LENGTH: 32
<212> TYPE: DNA
<213> ORGANISM: Homo sapiens

<400> SEQUENCE: 11
tacaggaaaa attgggaagc ctgaatctgc gg                           32

<210> SEQ ID NO 12
<211> LENGTH: 35
<212> TYPE: DNA
<213> ORGANISM: Homo sapiens

<400> SEQUENCE: 12
tggcaggagg tctgcaaaca gctgtcagac agaaa                        35

<210> SEQ ID NO 13
<211> LENGTH: 32
<212> TYPE: DNA
<213> ORGANISM: Homo sapiens

<400> SEQUENCE: 13
acagatgcca gtattctaca ggaaaaattg gg                           32

<210> SEQ ID NO 14
<211> LENGTH: 32
<212> TYPE: DNA
<213> ORGANISM: Homo sapiens

<400> SEQUENCE: 14
gatgccagta ttctacagga aaaattggga ag                           32

<210> SEQ ID NO 15
<211> LENGTH: 32
<212> TYPE: DNA
<213> ORGANISM: Homo sapiens

<400> SEQUENCE: 15
aagcctgaat ctgcggtggc aggaggtctg ca                           32
```

```
<210> SEQ ID NO 16
<211> LENGTH: 22
<212> TYPE: DNA
<213> ORGANISM: Homo sapiens

<400> SEQUENCE: 16
ctgcggtggc aggaggtctg ca                                              22

<210> SEQ ID NO 17
<211> LENGTH: 22
<212> TYPE: DNA
<213> ORGANISM: Homo sapiens

<400> SEQUENCE: 17
aagcctgaat ctgcggtggc ag                                              22

<210> SEQ ID NO 18
<211> LENGTH: 22
<212> TYPE: DNA
<213> ORGANISM: Homo sapiens

<400> SEQUENCE: 18
tgaatctgcg gtggcaggag gt                                              22

<210> SEQ ID NO 19
<211> LENGTH: 32
<212> TYPE: DNA
<213> ORGANISM: Homo sapiens

<400> SEQUENCE: 19
tgcagacctc ctgccaccgc agattcaggc tt                                   32
```